US012767620B2

(12) United States Patent
Oneal

(10) Patent No.: US 12,767,620 B2
(45) Date of Patent: Oct. 20, 2026

(54) SYSTEM, APPARATUS, AND METHOD FOR HYDROCARBON PROCESSING

(71) Applicant: Enerflex US Holdings Inc., Houston, TX (US)

(72) Inventor: Timothy W. Oneal, Tulsa, OK (US)

(73) Assignee: Enerflex US Holdings Inc., Houston, TX (US)

( * ) Notice: Subject to any disclaimer, the term of this patent is extended or adjusted under 35 U.S.C. 154(b) by 204 days.

(21) Appl. No.: 18/539,085

(22) Filed: Dec. 13, 2023

(65) Prior Publication Data

US 2024/0300873 A1 Sep. 12, 2024

Related U.S. Application Data

(63) Continuation of application No. 17/705,096, filed on Mar. 25, 2022, now Pat. No. 11,884,621.

(Continued)

(51) Int. Cl.

*B01D 3/14* (2006.01)
*B01D 3/00* (2006.01)

(Continued)

(52) U.S. Cl.

CPC ................ *C07C 7/09* (2013.01); *B01D 3/007* (2013.01); *B01D 3/143* (2013.01); *C07C 7/005* (2013.01);

(Continued)

(58) Field of Classification Search

CPC .. C07C 7/09; C07C 7/005; C07C 9/04; B01D 3/007; B01D 3/143; C10L 3/10

See application file for complete search history.

(56) References Cited

U.S. PATENT DOCUMENTS

| | | | | |
|---|---|---|---|---|
| 4,854,955 | A | 8/1989 | Campbell et al. | |
| 4,976,849 | A * | 12/1990 | Soldati .................. | F25J 3/0242 62/631 |

(Continued)

FOREIGN PATENT DOCUMENTS

| | | | |
|---|---|---|---|
| AU | 2003230778 | B2 | 6/2007 |
| CA | 2614404 | C | 5/2011 |
| WO | 2019078892 | A1 | 4/2019 |

OTHER PUBLICATIONS

International Preliminary Report on Patentability issued in PCT Application No. PCT/US2022/022029; mailed Oct. 5, 2023 [12 pages].

(Continued)

*Primary Examiner* — Jonathan Miller

(74) *Attorney, Agent, or Firm* — Alberto Q. Amatong, Jr.; Amatong McCoy LLC

(57) ABSTRACT

A process for the separation of a natural gas stream is provided. The process includes receiving an effluent gas flow from a first fractionator operating at a first pressure, splitting the effluent gas flow into a first stream and a second stream, and passing the first stream through a heat exchanger thereby causing a phase change of at least a portion of the first stream from a gaseous state to a liquid state. The process includes inserting the first stream into an upper portion of a second fractionator operating at a second pressure. The second pressure is lower than the first pressure. The process includes inserting the second stream into a lower portion of the second fractionator, and diverting liquids from a lower portion of the second fractionator to the first fractionator.

22 Claims, 7 Drawing Sheets

Related U.S. Application Data

(60) Provisional application No. 63/166,179, filed on Mar. 25, 2021.

(51) Int. Cl.

*C07C 7/00* (2006.01)
*C07C 7/09* (2006.01)
*C07C 9/04* (2006.01)
*C10L 3/10* (2006.01)
*F25J 1/00* (2006.01)

(52) U.S. Cl.

CPC *C07C 9/04* (2013.01); *C10L 3/10* (2013.01); *F25J 1/0022* (2013.01)

(56) References Cited

U.S. PATENT DOCUMENTS

| | | | | |
|---|---|---|---|---|
| 5,372,009 | A * | 12/1994 | Kaufman | F25J 3/0233 62/935 |
| 5,546,764 | A * | 8/1996 | Mehra | C10G 70/06 62/938 |
| 7,257,966 | B2 | 8/2007 | Lee et al. | |
| 7,793,517 | B2 | 9/2010 | Patel et al. | |
| 8,303,848 | B2 * | 11/2012 | Morita | C01B 3/384 252/373 |
| 8,919,148 | B2 | 12/2014 | Wilkinson et al. | |
| 9,192,876 | B2 * | 11/2015 | Amin | B01D 3/36 |
| 9,376,356 | B2 * | 6/2016 | Iijima | C07C 29/1518 |
| 9,434,657 | B2 | 9/2016 | Onishi et al. | |
| 10,227,273 | B2 | 3/2019 | Miller et al. | |
| 10,520,249 | B2 * | 12/2019 | Horne | C10L 3/12 |
| 11,112,175 | B2 | 9/2021 | Mak | |
| 11,884,621 | B2 * | 1/2024 | Oneal | F25J 3/0233 |
| 2003/0029190 | A1 * | 2/2003 | Trebble | F25J 3/0242 62/620 |
| 2008/0168797 | A1 * | 7/2008 | Mak | B01D 19/00 62/619 |
| 2009/0107175 | A1 | 4/2009 | Patel et al. | |
| 2012/0232172 | A1 | 9/2012 | Tasaka et al. | |
| 2012/0233920 | A1 * | 9/2012 | Amin | C07C 7/05 48/127.3 |
| 2012/0277497 | A1 * | 11/2012 | Lee | C07C 67/08 568/885 |
| 2014/0060114 | A1 | 3/2014 | Mak | |
| 2015/0073195 | A1 | 3/2015 | Lynch et al. | |
| 2015/0353454 | A1 * | 12/2015 | Iijima | C01B 3/38 422/162 |
| 2017/0211877 | A1 * | 7/2017 | Horne | F25J 3/0238 |
| 2019/0128600 | A1 | 5/2019 | Yamamori et al. | |
| 2019/0154333 | A1 | 5/2019 | Mak | |
| 2022/0306553 | A1 * | 9/2022 | Oneal | F25J 3/0242 |
| 2024/0300873 | A1 * | 9/2024 | Oneal | C07C 9/04 |

OTHER PUBLICATIONS

International Search Report and Written Opinion mailed Aug. 3, 2022 (issued in PCT Application No. PCT/US22/22029) [16 pages].

International Search Report and Written Opinion mailed Jan. 17, 2025 (issued in PCT Application No. PCT/US2024/048993) [20 pages].

Ortloff Engineers, Ltd., Retro-Flex Plus, Accessed on May 24, 2022, 2 pages total.

Pierce, M.C.; Cuellar, K.T.; Lynch J.T.; Peyton, J.A.; Miller, S.A., 5th Generation NGL/LPG Recovery Technologies for Retrofits, 96th Annual GPA Midstream Convention, Apr. 11, 2017, pp. 1-13, Ortloff Engineers, Ltd., Midland, US.

Pitman, R.N., Hudson, H.M., Wilkinson, J.D., Cuellar, K.T., Next Generation Processes for NGL/LPG Recovery, 77th Annual Convention of the Gas Processors Association, Mar. 16, 1998, Ortloff Engineers, Ltd., Midland, U.S.

Shatla, A.K., Abdelwaly, A.A., Retrofit an LPG plant for improved output and ethane recovery, Gas Processing & LNG, Accessed on May 24, 2022, 8 pages, Gulf Publishing Holdings, LLC, Cairo, Egypt.

International Preliminary Report on Patentability issued in PCT Application No. PCT/US24/48993; mailed Apr. 9, 2026 [17 pages].

* cited by examiner

SYSTEM, APPARATUS, AND METHOD FOR HYDROCARBON PROCESSING

CROSS-REFERENCE TO RELATED APPLICATIONS

The present application claims the benefit of U.S. Provisional Patent Application No. 63/166,179, filed on Mar. 25, 2021, entitled "System, Apparatus, and Method for Hydrocarbon Processing," the entirely of which is incorporated herein by reference, for all purposes, and made a part of the present disclosure.

BACKGROUND

This present disclosure relates, generally, to hydrocarbon processing, and, more directly, to a system, apparatus, and method for the separation of fluids (gas or liquid) containing hydrocarbons. More specifically, the disclosed system, apparatus, and method are particularly relevant to separation and recovery techniques in natural gas liquid/liquid petroleum gas (NGL/LPG) processing systems. In that respect, systems, apparatus, and methods disclosed herein are particularly suited or applicable to the separation of ethane, propane, and/or heavier hydrocarbon from such fluid streams.

BRIEF SUMMARY

Some embodiments of the present disclosure include a process for separating a natural gas stream. The process includes directing a first portion of an input stream into a first fractionator. The input stream includes natural gas. The process includes fractionating the input stream within the first fractionator. Fractionating the input stream within the first fractionator forms a product stream and a first vapor effluent stream. The process includes directing the first vapor effluent stream into a second fractionator. The process includes fractionating the first vapor effluent stream within the second fractionator. Fractionating the first vapor effluent stream within the second fractionator forms a first liquid stream and a second vapor effluent stream. The process includes directing the first liquid stream into the first fractionator and fractionating the first liquid stream within the first fractionator while fractionating the input stream within the first fractionator.

Some embodiments of the present disclosure include a system for separating a natural gas stream. The system includes a natural gas inlet and a first fractionator including one or more inlets. At least one of the inlets of the first fractionator is in fluid communication with the natural gas inlet. The first fractionator includes a first vapor effluent outlet and a first liquid product outlet. The system includes a second fractionator. The second fractionator includes one or more inlets in fluid communication with the first vapor effluent outlet. The second fractionator includes a second vapor effluent outlet and a second liquid product outlet. The second liquid product outlet is in fluid communication with at least one of the inlets of the first fractionator.

Some embodiments of the present disclosure include a method for retrofitting a natural gas separation plant that includes a natural gas inlet and a first fractionator including one or more inlets, where at least one of the inlets of the first fractionator is in fluid communication with the natural gas inlet, and where the first fractionator includes a first vapor effluent outlet and a first liquid product outlet. The method includes providing a second fractionator. The second fractionator includes one or more inlets, a second vapor effluent outlet, and a second liquid product outlet. The method includes fluidly coupling at least one inlet of the second fractionator with the first vapor effluent outlet. The method includes fluidly coupling the second liquid product outlet with at least one of the inlets of the first fractionator.

Some embodiments of the present disclosure include a process for the separation of a gas stream. The process includes receiving an effluent gas flow from a first fractionator operating at a first pressure. The process includes splitting the effluent gas flow into a first stream and a second stream. The process includes passing the first stream through a heat exchanger thereby causing a phase change of at least a portion of the first stream from a gaseous state to a liquid state. The process includes inserting the first stream into an upper portion of a second fractionator operating at a second pressure. The second pressure is lower than the first pressure. The process includes inserting the second stream into a lower portion of the second fractionator. The process includes diverting liquids from a lower portion of the second fractionator to the first fractionator.

Some embodiments of the present disclosure include a process for the separation of a gas stream. The process includes directing an effluent gas flow from a first fractionator, and subjecting a portion of the effluent gas flow to a heat exchange. The process includes directing a stream containing at least a portion of said effluent gas flow into a second fractionator. The process includes directing a stream containing liquids from the second fractionator to the first fractionator.

Some embodiments of the present disclosure include a process for the separation of a gas stream. The process includes drawing a stream containing liquids from a secondary fractionator to a main fractionator. The process includes splitting effluent gas flow from the secondary fractionator into a first stream and a second stream. The process includes compressing the second stream prior to directing said compressed stream to the secondary fractionator.

Some embodiments of the present disclosure include a system for processing a natural gas stream for hydrocarbon recovery. The system includes a main fractionator, a secondary fractionator, and an effluent flow line directed as an outlet of the main fractionator. The effluent line is divided into a first flow line and a second flow line. A first heat exchanger is in fluid communication with the first flow line and intermediate the main and secondary fractionators such that a first stream exiting said heat exchanger discharges into an upper portion of the secondary fractionator. The second flow line communicates a second stream from the effluent flow into a lower portion of the secondary fractionator. A lower portion of the second fractionator is disposed in fluid communication with the first fractionator such that a stream containing fluids is communicated from the lower portion to the main fractionator.

Some embodiments of the present disclosure include a system for processing a natural gas stream for hydrocarbon recovery. The system includes a main fractionator, a secondary fractionator, and a first effluent flow line directed from the main fractionator. The first effluent flow line is configured to discharge into to a lower portion of the secondary fractionator. A second effluent flow line is directed from an effluent outlet of the secondary fractionator. The second effluent line is divided into a first flow line and a second flow line in fluid communication with an upper portion of the secondary fractionator. A compressor is disposed in the second flow line downstream of said effluent outlet. A first heat exchanger is disposed in fluid communication with the second flow line and intermediate the effluent outlet and an inlet into an upper portion of the secondary fractionator such that a first stream exiting the first heat exchanger discharges into an upper portion of the secondary fractionator via said inlet. The second flow line communicates a second stream from the effluent outlet into a lower portion of the secondary fractionator. A lower portion of the secondary fractionator is disposed in fluid communication with the main fractionator, such that a stream containing fluids is communicated from the lower portion of the secondary fractionator to the main fractionator.

BRIEF DESCRIPTION OF THE DRAWINGS

So that the manner in which the features and advantages of the systems, configurations, constructions, apparatus, process, techniques, and/or methods of the present disclosure may be understood in more detail, a more particular description may be had by reference to specific implementations that are illustrated in the appended drawings. It is noted, however, that the drawings are simplified schematics and flow diagrams showing specific implementations for illustration and are, therefore, not to be considered limiting of the disclosed concepts, which include other effective applications as well. It is noted, for example, that certain applications may employ less than all of the different aspects described below.

DETAILED DESCRIPTION

Figure 1:
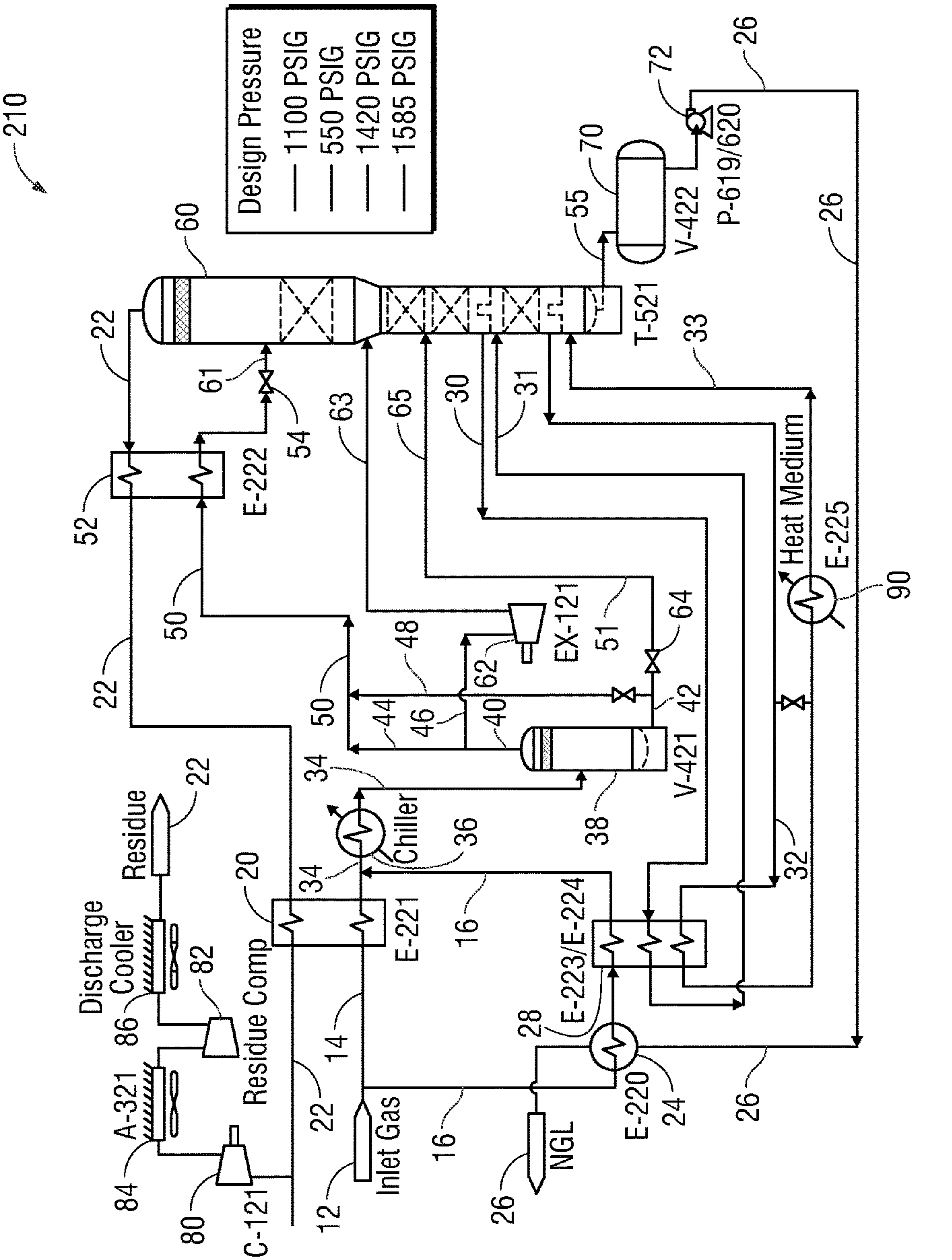
FIG. 1 is a schematic and flow diagram illustrating a prior art system for natural gas processing, including the recovery of propane and heavier hydrocarbons from a natural gas stream.

The present disclosure includes systems and methods for the separation of fluid steams containing hydrocarbons, including the separation of ethane, propane, and/or heavier hydrocarbon from NGL and LPG streams. Natural gas liquids (NGLs) contain propane, butane, and other hydrocarbons. NGLs can have a higher value as a separate product and are, thus, often separated from natural gas streams. Moreover, reducing the concentration of higher hydrocarbons and water in the stream reduces or prevents the formation of hydrocarbon liquids and hydrates in pipelines carrying natural gas.

The separation of NGL from natural gas is typically performed at a centralized processing plant using a process that is similar to processes used to dehydrate natural gas. Common techniques for removing NGL from a natural gas stream include the absorption process and the cryogenic expander process.

Once NGL is removed from a natural gas stream, the NGL can be fractionated into various constituents, such as propane, butane, and other hydrocarbons, which can, optionally, be sold as relatively high-purity products. Fractionation of NGL can be performed at a centralized processing plant where the NGL is removed from the natural gas stream, or can be performed downstream, such as in a regional NGL fractionation center. As is generally known, fractionation entails heating a mixed NGL stream and processing this NGL stream through a series of distillation towers. The process may require passing the NGL stream through a series of distillation columns (or towers), and relying on the differences in the boiling points of the constituents, to separate out various components of the NGL stream into discrete streams (product streams). For example, an initial NGL stream may be directed into a first distillation column of a series of distillation columns, where the stream is heated such that the lightest (lowest boiling point) component(s) of the NGL boil within the first distillation column and exit the first distillation column as a first overhead vapor. Thus, the lightest, lowest boiling point components of the NGL can be separated from the remainder of the NGL stream in the first distillation column. The first overhead vapor can then be condensed to form a first product stream containing the lightest, lowest boiling point components of the NGL stream, which can be stored in a first product storage (e.g., a tank). In some embodiments, a portion of the condensed, first overhead vapor is used as a reflux in the first distillation column, and a remaining portion of the condensed, first overhead vapor is stored as a first product stream. By passing the stream through the first distillation column, the weight percent of some components within the stream can be reduced. For example, if it is desired to target removal of a first component (e.g., methane), the stream passed through and exiting the first column may be found to contain more, or a higher concentration, of the first component than the initial stream (fed into the column). The portion or remainder of the NGL stream that does not boil in this first distillation column will be found to contain more of the relatively heavier components than the initial stream. This portion can then be passed from the bottom of the first distillation column to a second distillation column, where the process may be repeated to form a second product stream. The produced second product stream will then contain a higher concentration of the relatively heavier NGL components than the previous or first product stream. The process of passing the NGL stream through a distillation column can be repeated a desired number times until the desired product streams are extracted from the NGL stream. Each successive distillation column can extract a product stream that contains higher concentrations of relatively heavier components, than the products streams from prior or upstream distillation column. Notably, the product streams from a distillation column may be passed through an additional distillation column or the same column for additional refinement of the products, as desired.

FIG. 1 depicts a natural gas processing and recovery system and process in accordance with the state of the art, to which the present disclosure relates. To illustrate and highlight certain concepts and structures introduced herein, various systems, subsystems, methods, processes, subprocesses, techniques, configurations, and constructions are introduced in the context of, or as modifications or improvements to, the system and process of FIG. 1.

With reference to FIG. 1, expander-based NGL recovery plant 210 is configured to separate ethane and propane from a gas stream using a Gas Subcooled Process (GSP). Plant 210 receives inlet stream 12. Inlet fluid stream 12 can be a natural gas fluid stream (also referred to as a feed stream). Inlet fluid stream 12 contains a mixture of compounds, such as ethane, propane, and other hydrocarbons. Inlet fluid stream 12 may contain compounds that are desirable in a product stream 26, such as ethane and/or propane, and may also contain compounds that are undesirable in the product stream 26 of the plant 210, such as hydrocarbons other than ethane and propane. For example, the presence of some compounds in the product stream 26, at least above a certain concentration level within the product stream, may cause the product stream 26 to not meet certain specifications. The plant 210 is configured to separate out compounds from the inlet fluid stream 12 to produce the product stream 26, such that the product stream 26 does not contain the undesirable compounds, or at least contains a concentration of the undesirable compounds that is below a certain threshold concentration. Additionally, the plant 210 can be configured to dehydrate compounds in the inlet fluid stream 12 to prevent hydrate (ice) formation under cryogenic conditions.

The inlet fluid stream 12 is split into two streams-a first fluid stream 14 and a second fluid stream 16. First fluid stream 14 is directed through a first heat exchanger 20. Within the first heat exchanger 20, the first fluid stream 14 is passed in thermal communication with a residue gas stream 22, such that heat transfer occurs between the first fluid stream 14 and the residue gas stream 22. Passing the first fluid stream 14 through the first heat exchanger 20 cools the first fluid stream 14, such that the portion of the first fluid stream 14 exiting the first heat exchanger 20 is at a lower temperature than the portion of the first fluid stream 14 entering the first heat exchanger 20.

The second fluid stream 16 is directed through a second heat exchanger 24, where it is passed in thermal communication with an NGL stream 26 (i.e., effecting heat transfer between the second fluid stream 16 and the NGL stream 26). In this way, the second fluid stream 16 cools, and exits the second heat exchanger 24 at a lower temperature than at entry.

The second fluid stream 16 exiting the second heat exchanger 24 then flows through a third heat exchanger 28. Within the third heat exchanger 28, the second fluid stream 16 is in thermal communication with a first reboiler stream 30 and a second reboiler stream 32, such that heat transfer occurs between the second fluid stream 16 and the reboiler streams 30 and 32. Passing the second fluid stream 16 through the third heat exchanger 28 cools the second fluid stream 16, such that the portion of the second fluid stream 16 exiting the third heat exchanger 28 is at a lower temperature than the portion of the second fluid stream 16 entering the third heat exchanger 28. While heat exchange between the second fluid stream 16 and the reboiler streams 30 and 32 is depicted as occurring in a single heat exchanger, in embodiments of the present disclosure calling for similar treatment of reboiler streams, the desired heat exchange may be achieved through separate heat exchangers (e.g., in series or parallel)). The contents of the reboiler streams 30 and 32 can vary depending on the amount of ethane that is being rejected. The stripping vapors 31 and 33 formed by the reboiler streams strip methane and ethane (in rejection mode) within the fractionator 60. The stripping vapor 31 can contain, for example, $C_1$ (e.g., 44%), $C_2$ (e.g., 23%), $C_3$ (e.g., 18%), $C_4$ (e.g., 9%), <2% inerts, and a remainder of $C_5$ or heavier (all mole %). The stripping vapor 31 may be or not be fully vaporized. The stripping vapor 33 can contain, for example, $C_1$ (e.g., 0.7 to 4%), $C_2$ (e.g., 45 to 55%), $C_3$ (e.g., 35 to 43%), $C_4$ (e.g., 6 to 7%), <0.7% inerts, and a remainder $C_5$ or heavier components (all mole %).

First and second fluid streams 14 and 16 are then recombined to form combined stream 34. While the first and second fluid streams 14 and 16 are shown as being separated, then separately cooled, and then recombined, in embodiments of the present disclosure, the inlet fluid stream 12 is cooled without being separated.

Referring again to FIG. 1, combined stream 34 passes through chiller 36 and cooled. The cooled combined stream 34 then passes into separator 38 (a cold separator, where the combined stream 34 is separated into a vapor stream 40 and a condensed liquid stream 42. The contents of the vapor stream 40 and the condensed liquid stream 42 is, at least partially, dependent on the composition of the inlet gas 12 and the temperature and pressure of the separator 38. In one example, the vapor stream 40 contains from 80 to 85% by mole methane and inert components, from 9 to 12% by mole ethane, and about 3.5% by mole propane and a minor amount of heavies. In one example the condensed liquid stream 42 contains from 40 to 45% by mole methane, from 1 to 2% by mole inert components, from 20 to 25% by mole ethane, from 15 to 20% by mole propane, from 5 to 10% by mole butane, and about 4% by mole heavies.

The vapor stream 40 is discharged from the separator 38 and is divided into a first vapor stream 44 and a second vapor stream 46, whereas the condensed liquid stream 42 is divided into a first liquid stream 48 and a second liquid stream 51. The first vapor stream 44 is then combined with the first liquid stream 48, forming a combined stream 50. Combined stream 50 is passed through a fourth heat exchanger 52. Within the fourth heat exchanger 52, the combined stream 50 is in thermal communication with the residue gas stream 22, such that heat transfer occurs between the combined stream 50 and the residue gas stream 22. Passing the combined stream 50 through the fourth heat exchanger 52 cools the combined stream 50, such that the portion of the combined stream 50 exiting the fourth heat exchanger 52 is at a lower temperature than the portion of the combined stream 50 entering the fourth heat exchanger 52. Additionally, within the fourth heat exchanger 52, at least a portion of the combined stream 50 is condensed. The condensed combined stream 50 then passes through expansion valve 54. Within expansion valve 54, the condensed combined stream is flash expanded to a pressure above an operating pressure of fractionator 60, forming reflux stream 61. After exiting the expansion valve 54, the first reflux stream 61 is supplied to the fractionator 60.

Returning to the discharge of separator 38, the second vapor stream 46 is passed to an expander-booster compressor combination or turboexpander 62. Within the turboexpander 62, mechanical energy is extracted from the relatively high-pressure feed of the second vapor stream 46. The turboexpander 62 expands the second vapor stream 46 such that the second vapor stream 46 is brought to a pressure that is within the range of the operating pressure(s) of the fractionator 60. Within turboexpander 62, the second vapor stream 46 is also cooled, reducing a temperature of the second vapor stream 46 and forming second reflux stream 63. The second reflux stream 63 is supplied to the fractionator 60. The second reflux stream 63 is supplied to the fractionator 60 at a position that is below the position where the first reflux stream 61 is supplied to the fractionator 60.

From separator 38, the second liquid stream 51 is directed through an expansion valve 64 to form a third reflux stream 65. This lowers the pressure of the second liquid stream 51 to a pressure that is within the range of the operating pressure(s) of the fractionator 60, while also cooling the second liquid stream 51. Meanwhile, the third reflux stream 65 is supplied to the fractionator 60—at a position that is below the position where the second reflux stream 63 is supplied to the fractionator 60.

The fractionator 60 can operate as a demethanizer tower, and can be or include a conventional distillation column containing multiple, vertically spaced trays, one or more packed beds, or combinations thereof. Within the fractionator 60, components in the vapor phase rise upward and relatively colder components in the liquid phase fall downward. The trays and/or packing in the fractionator 60 provide for contact between vapor phase compounds (e.g., vapor phase within the second reflux stream 63) within the fractionator 60 rising upward and liquid phase compounds within the fractionator 60 falling downward, such that ethane, propane, butane, and heavier components condense and are absorb into the liquid phase within the fractionator 60.

Heat exchanger 28 heats and vaporizes the first and second reboiler streams 30 and 32 (of liquids from fractionator 60) to provide stripping vapors 31 and 33, respectively, to the fractionator 60. The stripping vapors 31 and 33 flow up within the column of the fractionator 60 and strip the liquid flowing down the fraction of methane and lighter components (i.e., the stripping vapors 31 and 33 function to remove methane and lighter components from the liquid). After passing through the heat exchanger 28, reboiler stream 32 flows through reboiler 90 to provide additional heat to the reboiler stream 32.

The liquid product 55 within the fractionator 60 is collected at a bottom of the fractionator 60 and provided to a natural gas surge tank 70, forming a liquid product stream, NGL stream 26. The NGL stream 26 is pumped, via a booster pump 72. For example, the NGL stream 26 can be pumped to storage, transport, or another location. Prior to exiting the plant 210, the NGL stream 26 flows through the second heat exchanger 24 to cool to the second fluid stream 16. While the fractionator disclosed herein is discussed in terms of having top, bottom, middle, lower, higher and other vertical, positional sections, one skilled in the art would understand that these designations and conventions have functional and processing relevance and do not limit the precise arrangement of the fractionators.

A vapor phase, residue gas stream 22, is withdrawn from the top of the fractionator 60. The residue gas stream 22 passes through the fourth heat exchanger 52 to exchange heat with the combined stream 50 and, downstream therefrom, passes through the first heat exchanger 20 to exchange heat with the first fluid stream 14. The residue gas stream 22 is then re-compressed in two stages via compressors 80 and 82. The residue gas stream 22 passes through compressor 80, through cooler 84, through compressor 82, and then through cooler 86. After being compressed and cooled, the residue gas stream 22 is discharged from the plant 210.

The above description of FIG. 1 provides a basic, prior art system and process for NGL processing and recovery, which is modified and/or improved upon as provided in the present disclosure and illustrated through the exemplary systems and methods of FIGS. 2-6 and the accompanying descriptions.

FIGS. 2-6 illustrate exemplary and localized systems, methods and configurations of natural gas processing and recovery, as incorporated within the system and process of FIG. 1, or as alternatives to the system and process of FIG. 1. FIG. 2-6 depict embodiments of a hydrocarbon processing plant, plants 10*a*-10*e*, that are similar to plant 210 described in respect to FIG. 1, but modified. Plants 10*a*-10*e* and plant 210 are different, as plants 10*a*-10*e* include and implements subsystems, subprocesses, techniques, and configurations in accordance with the present disclosure. Like elements amongst FIGS. 1-6 are referenced using like numerals. The subsystems or configurations shown in FIGS. 2-6 can, in some embodiments, be incorporated into an existing system (such as plant 210) via retrofitting the existing system.

In some embodiments disclosed herein, the relevant system or process is configured or operated to produce an NGL product stream having higher propane recovery and essentially free of ethane (ethane rejection mode). For example, the gas effluent from the fractionator 60 in FIG. 1, which forms the residue gas stream 22, contains propane not recovered into the liquid product 55 of the fractionator. At least a portion of the propane within the gas effluent from the fractionator 60 can be recovered by passing the gas effluent through a second fractionator (as shown in FIGS. 2-6). In further embodiments disclosed herein, systems and processes are configured and/or operated so as to reduce the occurrence of CO2 freeze and increase ethane recovery.

In some embodiments according to the present disclosure, the systems or processes are configured and operated to include retrieval of at least a portion of an existing effluent gas from a first fractionator (e.g., demethanizer or deethanizer tower) at a given pressure, of a natural gas plant, and providing the effluent gas into a bottom of a second fractionator tower operating at lower pressure than the first fractionator. The remaining effluent gas, may be passed through a heat exchanger and chilled to produce liquid that is fed to the top of the second fractionator tower. The effluent gas from the second fractionator forms the residue or final gas of the plant. Thus, in some applications, such as a GSP flow-scheme, a top fed, GSP reflux, can be diverted from the first fractionator to a bottom of the second fractionator at a lower pressure. The second fractionator contains liquids in a bottom that are suitable for reflux in the first fractionator. The second fractionator disclosed herein can operate at a lower pressure than the first fractionator. For example, in one embodiment the first fractionator (also referred to as the main fractionator) can operate at a pressure of from 200 psig to 300 psig or higher, and the second fractionator can operate at a pressure that is from 7 to 15 psi lower than the pressure of the first fractionator (e.g., the minimum pressure drop for the process).

Figure 2:
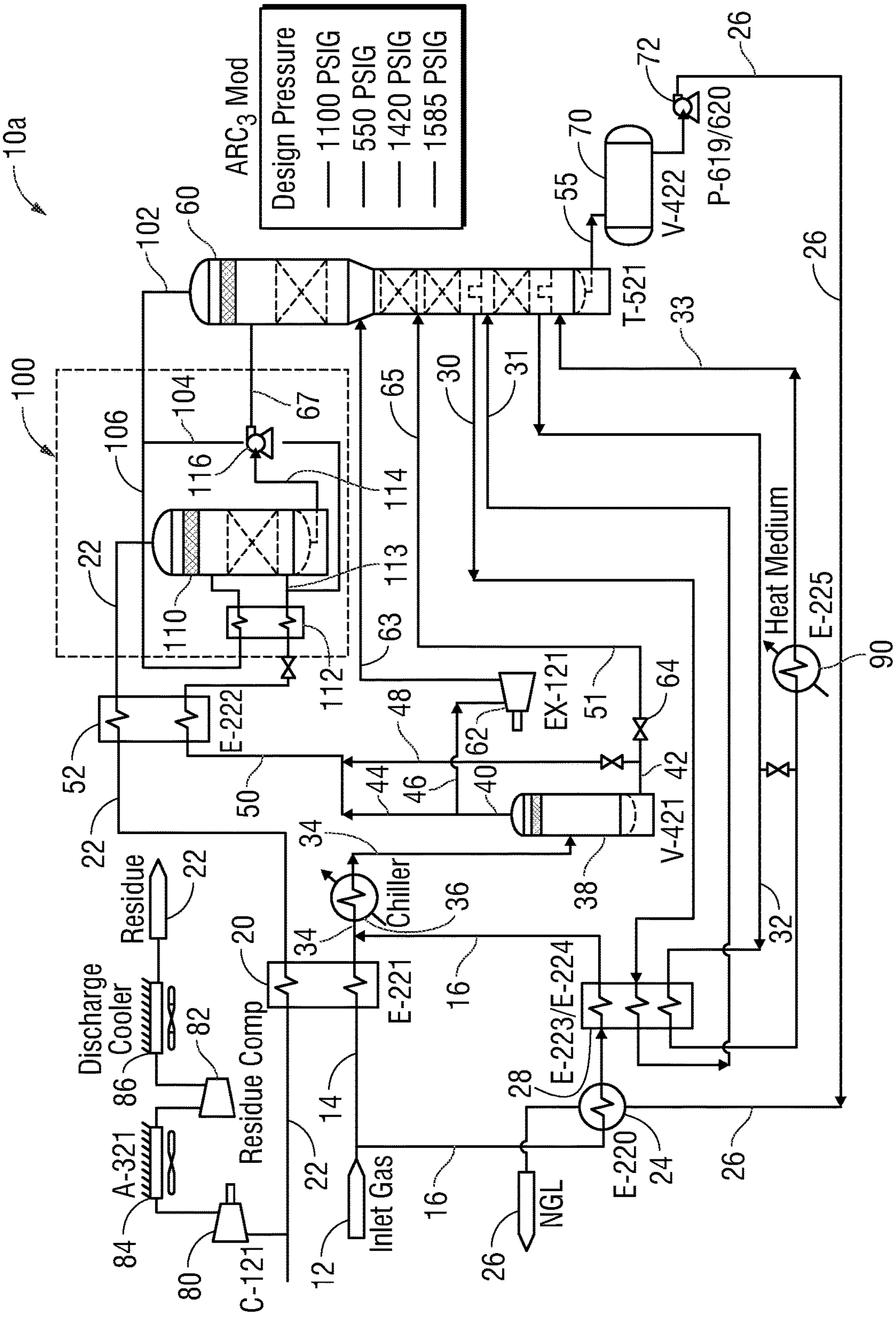
FIG. 2 is a schematic and flow diagram illustrating a system for natural gas processing, including the recovery of propane and heavier hydrocarbons from a natural gas stream, in accordance with embodiments of the present disclosure.

FIG. 2 depicts natural gas plant 10*a*. Natural gas plant 10*a* is similar to plant 210 shown in FIG. 1, but includes subsystem 100 incorporated therein to facilitate recovery of certain hydrocarbon components from natural gas, in accordance with the present disclosure. The techniques and system configuration illustrated in FIG. 2 may be implemented for the recovery of hydrocarbons such as ethane, propane, butane, or heavier hydrocarbons.

In the embodiment of FIG. 2, effluent gas stream 102 (which may be the same as stream 22 of FIG. 1) is withdrawn from the top end of the fractionator 60. The effluent gas stream 102 is then split into a first effluent gas stream 104 and a second effluent gas stream 106.

Combined stream 50, as previously described with reference to FIG. 0.1, exits the fourth heat exchanger 52 and passes through a fifth heat exchanger 112. Within the heat exchanger 112, the combined steam 50 is in thermal communication with the second effluent gas stream 106.

After exiting the heat exchanger 112, the combined stream 50 is combined with the first effluent gas stream 104 to form combined stream 113. The combined stream 113 is the fed to a bottom section of a second fractionator 110. In some embodiments, a diameter of the second fractionator is, generally, similar to that of the first fractionator. The second fractionator 110 can include a mass transfer device, such as packing and/or trays. Preferably, the effluent split is about 30% to about 80% flow to fractionator 110, more preferably, about 40%-80%, and normally, about 60%. That is, about 60% of effluent gas stream 102 forms first effluent gas stream 104 to be input into the second fractionator 110 as the bottom, and about 40% of effluent gas stream 102 forms second effluent gas stream 106 that is chilled and becomes a reflux to a top of the second fractionator 110.

The second effluent gas stream 106 is directed through the heat exchanger 112 (e.g., a brazed aluminum heat exchanger) where the second effluent gas stream 106 exchanges heat with the combined stream 50, such that the hotter second effluent gas stream 106 is cooled and the colder combined stream 50 is heated. From the heat exchanger 112, the second effluent gas stream 106 flows into a top section of the second fractionator 110. Typically, the second effluent gas stream 106 is at a temperature of about −90 to −145° F., depending on the temperature of the combined stream 50. Generally, the colder a reflux stream is, the higher recovery achieved with the product steam. Thus, the method preferably includes chilling of second effluent gas stream 106, which is the leanest stream in the plant 10*a*, to form a reflux to the top of the second fractionator 110 and crossing the second effluent gas stream 106 against the warmer portion of the first effluent gas stream 104 (as mixed with the combined stream 50) entering the bottom of the second new tower. The combination of the leanness of reflux formed by second effluent gas stream 106 and the temperatures and the mass transfer that is exchanged facilitates extraction of additional propane.

In some embodiments, the second fractionator 110 operates at a lower pressure than the pressure at which the fractionator 60 operates. Liquid within the second fractionator 110 is collected at the bottom end of the second fractionator 110, forming a liquid stream 114 that is withdrawn from the second fractionator 112 via pump 116. The pump 116 pumps the liquid stream 114 into the fractionator 60 as a reflux stream 67. The effluent (residue gas stream 22) is drawn from the top of the second fractionator 110.

Thus, relative to the plant 210 of FIG. 1, subsystem 100 includes an additional fractionator (section fractionator 110), an additional heat exchanger (heat exchanger 112), an additional pump (pump 116), and additional piping to connect these components. The subsystem 100 can be retrofitted into an existing system (e.g., plant 210), such as a GSP system. The subsystem 100 can also be added to cryogenic designs of other plant designs, such as EG Score, Recycle Split Vapor ("RSV"), legacy turboexpander plants without GSP reflux, or other designs. In some embodiments, the system 10*a*, with subsystem 100, the second fractionator 110 operates at pressure that is about 7 to 15 psi below the pressure at which the first fractionator 60 operates (which typically operates at about 200 to 350 psig or 200 to 270 psig depending upon how much ethane is targeted for recovery). The pressure at the inlet gas 12 is typically higher, such as from 850 to 1100 psi, until the separator 38. Downstream of the separator 38, JT valves and turboexpanders can be positioned to drop the flow(s) to the operating pressure of the fractionator 60, which can create at least some auto-refrigeration.

The temperature of the reflux of the second fractionator is typically colder than that of the first fractionator due to the ratio of volumes chilling the reflux and the leaner composition of the reflux in comparison to the stream chilling the reflux.

TABLE 1

TYPICAL OPERATING TEMPERATURES

| Case | Existing Demethanizer Tower Overheads (° F.) | Reflux to New (Second) Tower (° F.) | New Fractionator Tower Overheads (° F.) |
|---|---|---|---|
| 1 | −66 | −143 | −93 |
| 2 | −72 | −125 | −105 |
| 3 | −55 | −130 | −95 |
| 4 | −131 | −154 | −152 |

Table 2, below, illustrates differences in typical performance between the system and process discussed in respect to FIG. 1 and that of the embodiment discussed in respect to FIG. 2, when each respective plant is run in a deep rejection mode, prioritizing rejection of $C_2$ (e.g., 0% ethane recovery or substantially 0% ethane recovery). As can be seen, the embodiment in FIG. 2 offers an improvement of more than 6% more $C_3$ recovered, nearly 2% more isobutane ("i$C_4$") recovered, and more than 1% more normal butane ("n$C_4$") recovered when compared to the process used in FIG. 1. This difference in recovery percentages can result in significant economic advantages provided by the embodiment disclosed in FIG. 2. In addition, the embodiment discussed in FIG. 2 may reduce the probability of freezing attributable to CO2 while also increasing, incrementally, ethane recovery when the plant is in recovery mode. The percent recoveries disclosed herein are mole percent relative to the amount of the constituent in the inlet gas 12. For example, a 98% recovery of propane would mean that 98% of the propane in the inlet gas 12 is recovered in the liquid product 55.

TABLE 2

CHANGE IN PERFORMANCE IN DEEP REJECTION MODE

| | System of FIG. 1 | System of FIG. 2 | Change |
|---|---|---|---|
| Refrigeration Horsepower | 2,193 | 2,332 | 139 |
| Residue Horsepower | 18,378 | 19,084 | 706 |
| $C_2$ - % Recovered | 0.576 | 0.6185 | 0.0425 |
| $C_3$ - % Recovered | 91.6 | 98.31 | 6.71 |
| i$C_4$ - % Recovered | 98 | 99.93 | 1.93 |
| n$C_4$ - % Recovered | 98.86 | 99.98 | 1.12 |

Table 3, below, illustrates differences in typical performance of the system or process of FIG. 1 and the system or process discussed in respect to FIG. 2, when the two are operated in a typical rejection mode to achieve about 28% to 30% recovery of $C_2$. As shown, the embodiment of FIG. 2 offers an improvement of more than 4% more $C_3$ recovered, nearly 1% more iso butane ("i$C_4$") recovered, and more than 0.4% more normal butane ("$nC_4$") recovered when compared to the process used in FIG. 1. This difference in recovery percentages can result in significant economic advantages provided by the embodiment disclosed in FIG. 2.

TABLE 3

CHANGE IN PERFORMANCE IN REJECTION MODE

| | System of FIG. 1 | FIG. 2 Embodiment |
|---|---|---|
| Plant flow (MMscfd)* | 230 | 230 |
| % $C_2$ | 28.42 | 29.99 |
| % $C_3$ | 94.33 | 98.42 |
| % $iC_4$ | 98.98 | 99.91 |
| % $nC_4$ | 99.5 | 99.97 |
| Residue HP | 15,771 | 15,473 |
| Refrigeration HP | 2,915 | 4,115 |
| Total HP | 18,686 | 19,588 |

*MMscfd stand for Million Standard Cubic Feet per Day

Table 4, below, illustrates differences in typical performance between operation of the system and process discussed in respect to FIG. 1 and the embodiment discussed in respect to FIG. 2, when each plant is run in a slope recovery mode that operates at about 50% to 57% recovery of $C_2$. As shown, the embodiment of FIG. 2 offers an improvement of more than 3% more $C_3$ recovered, nearly 1% more iso butane ("$iC_4$") recovered, and more than 0.5% more normal butane ("$nC_4$") recovered. This difference in recovery percentages can result in significant economic advantages provided by the embodiment of FIG. 2.

TABLE 4

CHANGE IN PERFORMANCE IN RECOVERY MODE

| | System of FIG. 1 | FIG. 2 Embodiment |
|---|---|---|
| Plant flow (MMscfd) | 230 | 230 |
| % $C_2$ | 56.21 | 51.89 |
| % $C_3$ | 95.31 | 98.85 |
| % $iC_4$ | 98.95 | 99.94 |
| % $nC_4$ | 99.43 | 99.98 |
| Residue HP | 14,411 | 14,246 |
| Refrigeration HP | 4,170 | 4,303 |
| Total HP | 18,581 | 18,549 |

Figure 3:
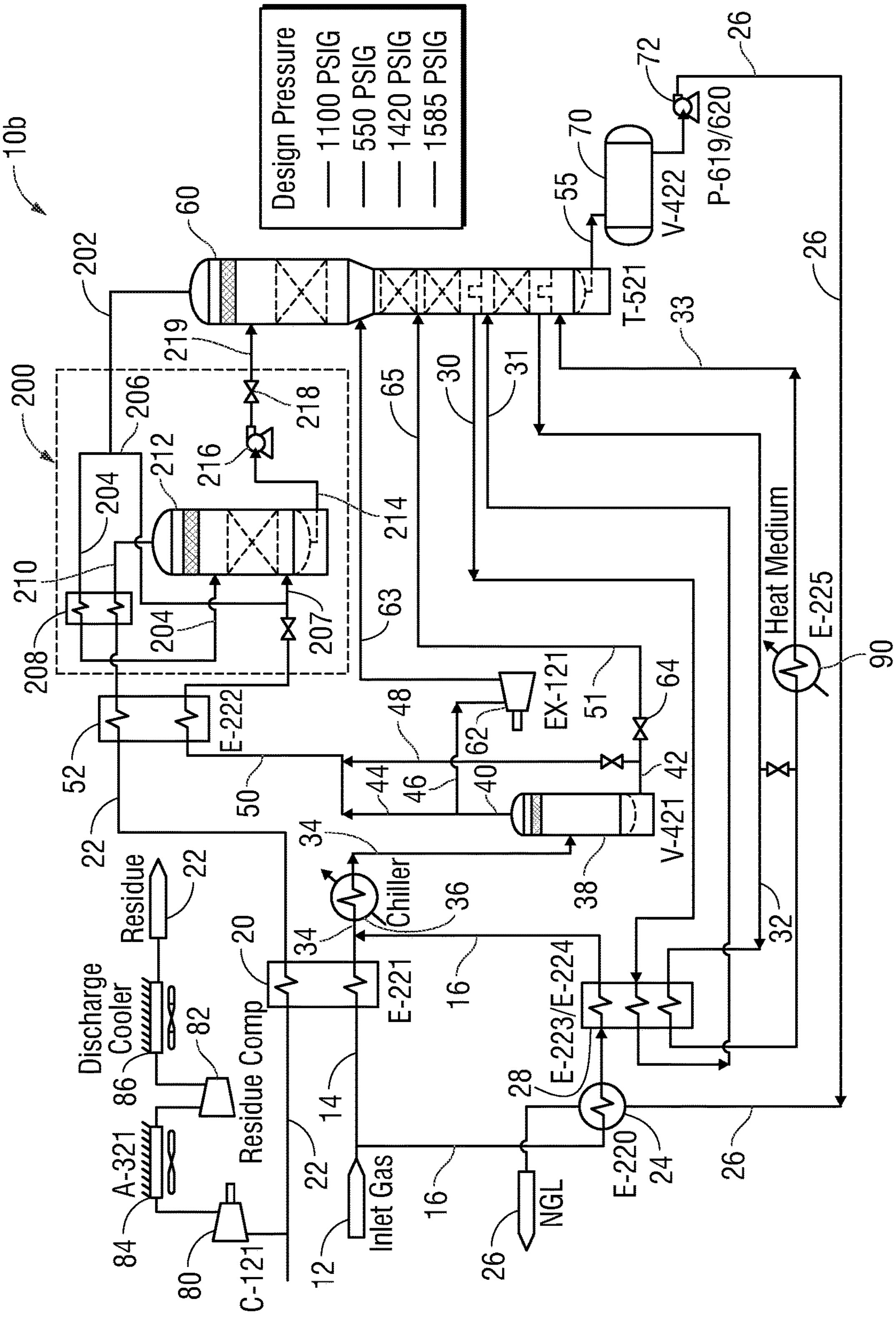
FIG. 3 is a schematic and flow diagram illustrating an alternative system for natural gas processing, including the recovery of propane and heavier hydrocarbons from a natural gas stream, in accordance with embodiments of the present disclosure.

Now turning to FIG. 3, a system and process is provided that illustrates modifications to a natural gas plant 10*b* to include a subsystem 200 facilitating recovery of certain hydrocarbon components from natural gas, according to the present disclosure. The techniques and system configuration illustrated may be implemented for the recovery of such hydrocarbons as ethane, propane, butane, or heavier hydrocarbons, as will become apparent to one of ordinary skill in the art.

In the embodiment of FIG. 3, effluent gas stream 202 (which may be the same as stream 22 of FIG. 1) exits the top of fractionator 60. The effluent gas stream 202 is split into a first flow stream 204 and a second flow stream 206. The first flow stream 204 is directed into a sixth heat exchanger 208, wherein the first flow stream 204 is passed in thermal communication with an effluent gas stream 210 from a second fractionator 212. With the heat exchanger 212, the first flow stream 204 is cooled and the effluent gas stream 210 from second fractionator 212 is heated. The first flow stream 204 then directed into a top section of the second fractionator 212. After exiting the heat exchanger 208, the effluent gas stream 210 becomes the residue gas stream 22.

The second flow stream 206 is combined with combined stream 50 (as discussed with respect to FIG. 1) and the resultant combined stream 207 is directed into the bottom section of second fractionator 212. In other embodiments, the second flow stream 206 flows directly into the second fractionator 212 without mixing with the combined stream 50. In some embodiments, the second flow stream 206 and/or the combined stream 50 flow into a top section of the second fractionator 212. The second fractionator 212 may operate at a lower pressure than the fractionator 60. As such, liquid in the second fractionator 212 is collected at the bottom of the second fractionator 212 to form a liquid stream 214 that is pumped via pump 216 into the fractionator 60 as a reflux stream 219. In some embodiments, the liquid stream 214 is pumped through an expander valve 218 to induce a phase change of at least some of the liquid stream 214—from the liquid phase to the gaseous phase prior to entering the fractionator 60. Thus, system 10*b* is the same as or substantially similar to system 10*a*, except that system 10*b* includes heat exchanger 208 which is positioned differently than heat exchanger 112 and that the liquid stream from the second fractionator passes through an expander valve 218 prior to entering the fractionator 60.

Figure 4:
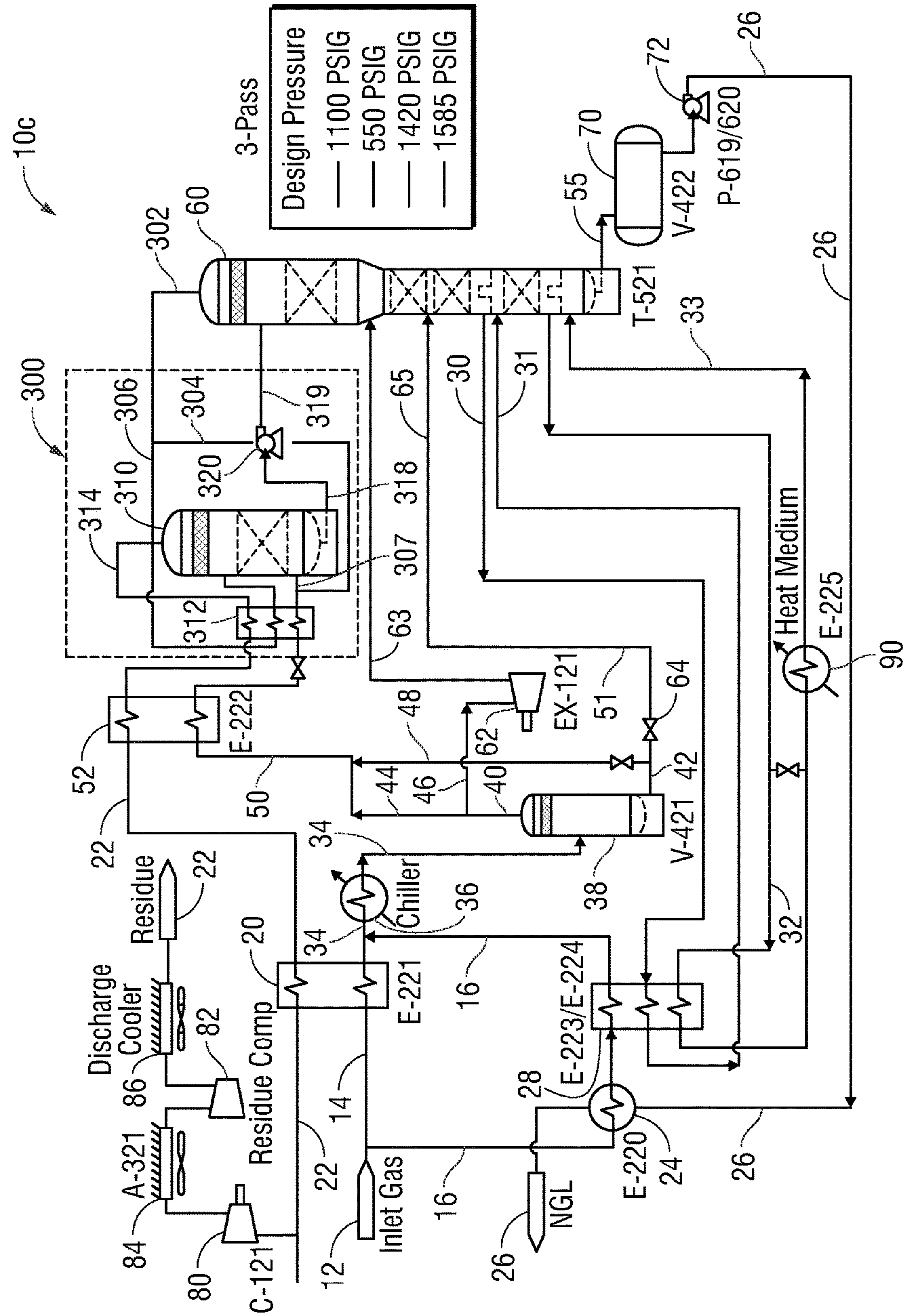
FIG. 4 is a schematic and flow diagram illustrating an alternative system for natural gas processing, including the recovery of propane and heavier hydrocarbons from a natural gas stream, in accordance with embodiments of the present disclosure.

FIG. 4 illustrates yet another system, method, and configuration for the processing of a natural gas liquid/liquid petroleum gas and the separation and recovery of certain hydrocarbons therefrom. As with the exemplary systems, methods, and configurations described above, important aspects are described and illustrated as modifications to the natural gas plant shown in FIG. 1. System 10*c* includes a subsystem 300 to facilitate recovery of certain hydrocarbon components from natural gas. The techniques and system configuration illustrated may be implemented for the recovery of such hydrocarbons as ethane, propane, butane, or heavier hydrocarbons, as will become apparent to one of ordinary skill in the art.

In the embodiment of FIG. 4, effluent gas stream 302 (which may be the same as stream 22 of FIG. 1) exits the top of fractionator 60 and is then split into a first effluent gas stream 304 and a second effluent gas stream 306. The first effluent gas stream 304 is introduced to combined stream 50 and form combined stream 307, before being passed to a bottom section of the second fractionator 310.

Meanwhile, the second effluent gas stream 306 is directed into a heat exchanger 312, through which effluent gas stream 314 from the top of second fractionator 310 and combined stream 50 also pass through. In this heat exchange, the second effluent gas stream 306 is cooled and then redirected to the top of the second fractionator 310. The effluent gas stream 314 from exiting the top of second fractionator 310 is heated to form the residue gas stream 22. Finally, the combined stream 50 is heated and then combined with the first effluent gas stream 304, prior to being passed to the bottom of the second fractionator 310.

In this embodiment, the second fractionator 310 may operate at a lower pressure than the fractionator 60. The liquid collected at the bottom of the second fractionator 310 is pumped, as liquid stream 318, by pump 320 into the fractionator 60 as reflux stream 319.

Figure 5:
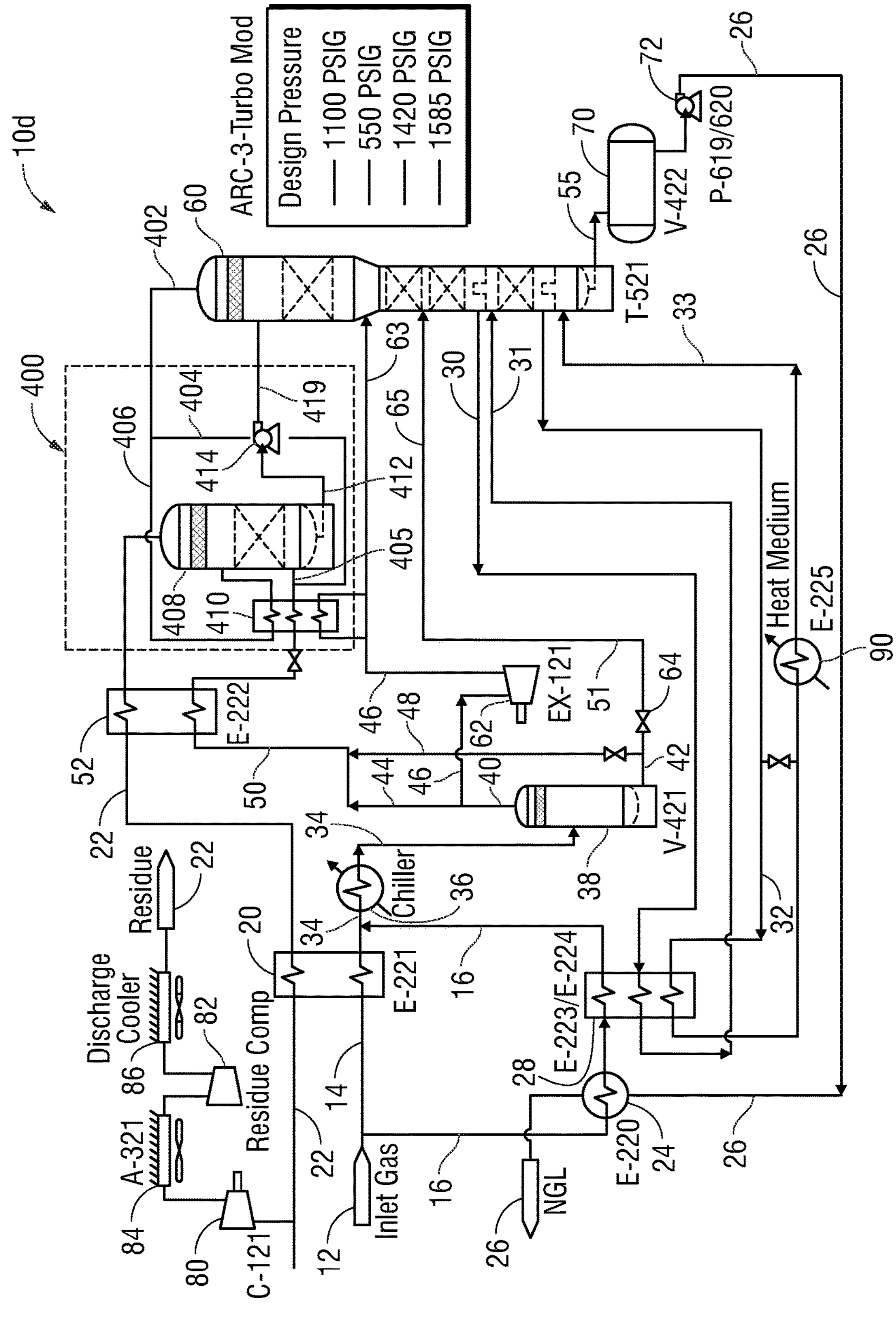
FIG. 5 is a schematic and flow diagram illustrating an alternative system for natural gas processing, including the recovery of propane and heavier hydrocarbons from a natural gas stream, in accordance with embodiments of the present disclosure.

FIG. 5 illustrates another exemplary system, method, and configuration according to the present disclosure including exemplary modifications to a natural gas plant. Plant 10*d* includes subsystem 400 to facilitate recovery of certain hydrocarbon components from natural gas. The techniques and system configuration illustrated may be implemented for the recovery of such hydrocarbons as ethane, propane, butane, or heavier hydrocarbons, as will become apparent to one of ordinary skill in the art.

In the embodiment of FIG. 5, an effluent gas stream 402 (which may be the same as stream 22 of FIG. 1) exits the top of the fractionator 60 and is then split into first effluent gas stream 404 and second effluent gas stream 406. The first effluent gas stream 404 is combined with combined stream 50 to form combined stream 405 before entering a bottom section of the second fractionator 408.

The second effluent gas stream 406 is directed into a heat exchanger 410 before being fed into the second fractionator 408. Each of the second effluent gas stream 406, the combined stream 50, and the second vapor stream 46 pass through the heat exchanger 410. Within the heat exchanger 410, the second effluent gas stream 406 is cooled prior to flowing into the second fractionator 408, the combined stream 50 is heated prior to combining with the first effluent gas stream 404 and flowing into the bottom of second fractionator 408, and the second vapor stream 46 is heated prior to flowing into the fractionator 60. From the bottom of the second fractionator 408, a liquid stream 412 is pumped back into the fractionator 60 via pump 414 as a reflux stream 419.

Figure 6:
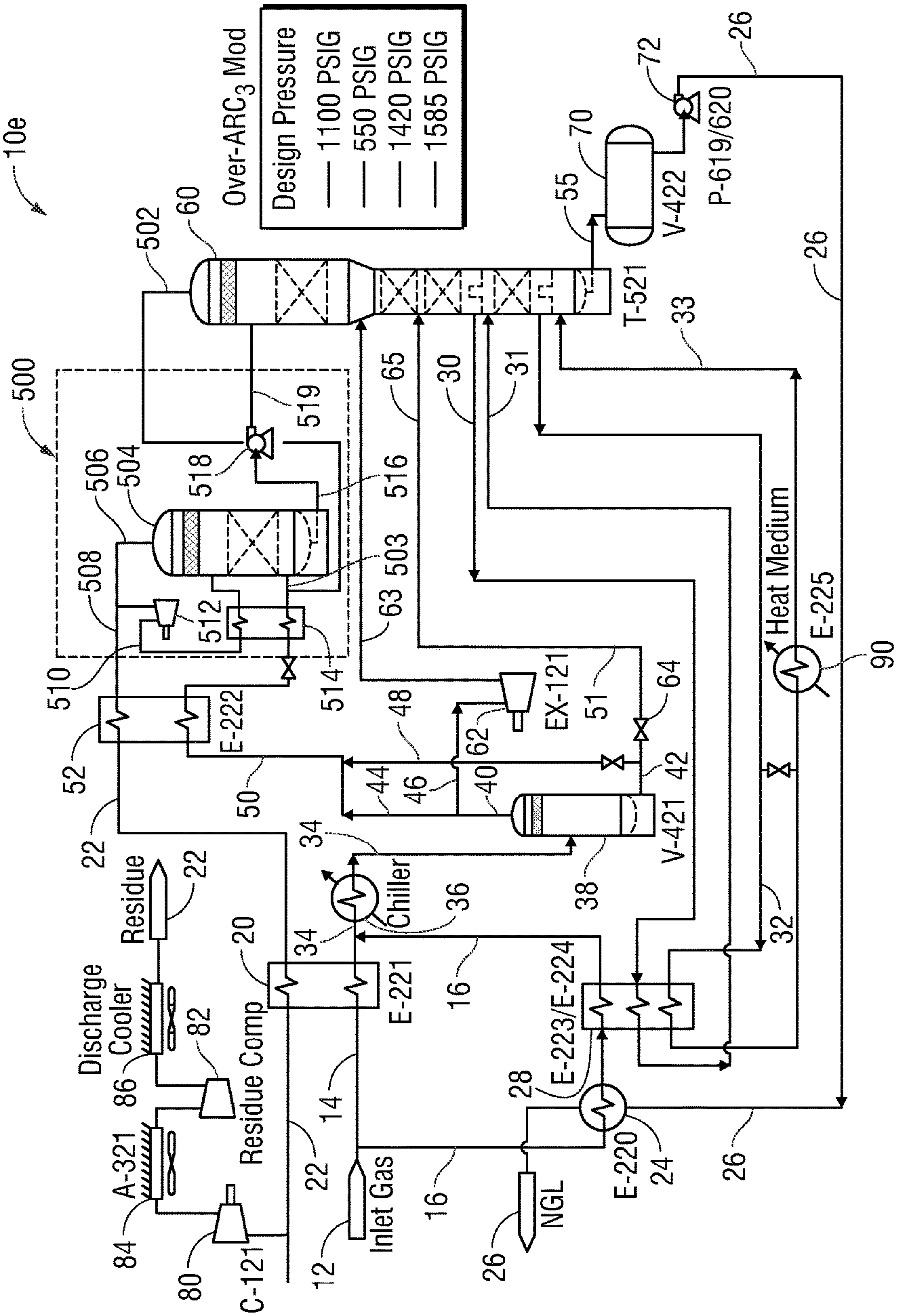
FIG. 6 is a schematic and flow diagram illustrating an alternative system for natural gas processing, including the recovery of propane and heavier hydrocarbons from a natural gas stream, in accordance with embodiments of the present disclosure.

FIG. 6 depicts another exemplary system, method, and configuration according to the present disclosure. FIG. 6 illustrates modifications to a natural gas plant 10*e* that includes a subsystem 500 to facilitate recovery of certain hydrocarbon components from natural gas, according to the present disclosure. The techniques and system configuration illustrated may be implemented for the recovery of such hydrocarbons as ethane, propane, butane, or heavier hydrocarbons, as will become apparent to one of ordinary skill in the art.

In the embodiment of FIG. 6, an effluent gas stream 502 (which may be the same as stream 22 of FIG. 1) exits the top of fractionator 60. Unlike the embodiments described in FIGS. 2-5, the effluent gas stream 502 is not split and/or directed to a heat exchanger, but is directed into the fractionator 60. The effluent gas stream 502 is combined with combined stream 50 to form combined stream 503. Combined stream 503 is directed into a bottom of the second fractionator 504. The second fractionator 504 produces a liquid stream 516, which is pumped via pump 518 into the fractionator 60 as a reflux stream 519.

An effluent gas stream 506 is drawn from the second fractionator 504 and split into a first effluent gas stream 508 and a second effluent flow stream 510. The first effluent flow stream 508 forms the residue gas stream 22 after passing through the heat exchanger 52. The second effluent gas stream 510 is compressed (e.g., the pressure of stream 510 can be increased by about 10 psi) via compressor 512. Compression of the second effluent gas stream 510 causes at least some of the stream 510 to phase change from a gaseous state to a liquid state prior to passing into heat exchanger 514. Within heat exchanger 514, the hotter stream 510 exchanges heat (thermal energy) with the colder combined stream 50, prior to the stream 510 moving into a top of the second fractionator 504. In addition, the compression of the stream 510 increases the heat transfer efficiency between the stream 510 and the stream 50 in the heat exchanger 514. The second fractionator 504 may operate at a lower pressure than the fractionator 60. By applying compression, and potentially air cooling before entering the heat exchanger 514, the reflux 510 can be colder and more condensed to enhance propane recovery.

Figure 7:
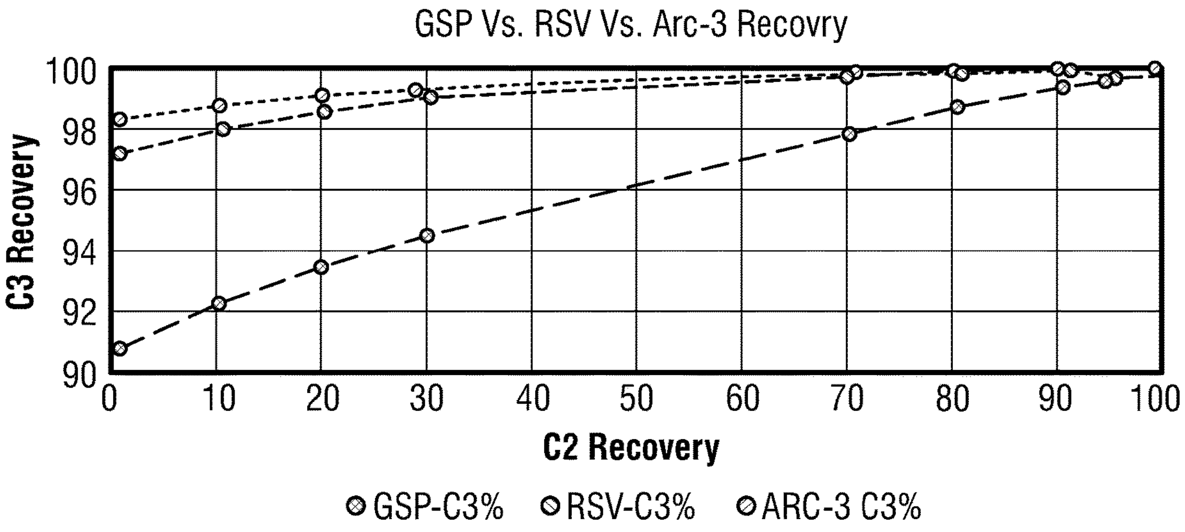
FIG. 7 is a graph propane recovery (y-axis) and ethane recovery (x-axis) for different processes.

FIG. 7 is a graph showing the propane recovery (y-axis) and ethane recovery (x-axis) for GSP (typical plants being retrofitted) vs. RSV (out of patent Orloff technology) vs. an embodiment of the present disclosure, ARC-3. From left to right on the graph, the $C_2$ recovery goes from deep rejection (no recovery/0% of ethane) up to a given plant types maximum recovery, generally 90-99%. Both the GSP and ARC-3 processes are limited to somewhere around 90-96% of ethane, whereas, the RSV process can achieve closer to 99% of ethane. The ARC-3 process provides for a steadier recovery and can, at some embodiments, achieve a higher recovery of propane at a given ethane value. The percent recoveries of RSV in FIG. 7 use a high residue gas pressure, which typically results in the highest incremental propane recoveries.

The RSV process is sensitive to residue gas pressure and the amount of recycle flowrate, all of which push recompression horsepower up. FIG. 7 shows an approximately 1200 #residue pressure, which has no impact on the performance of GSP or ARC-3. For the RSV, the amount of slip stream is approx. 15% of plant nameplate (the volume flow used for a reflux, i.e., 15% of available gas). Typically, the higher the flow %, the better the reflux and the better the recovery of propane. However higher flow requires more recompression, such that the recompression HP differential increases from about 20% to about 23 to 25% or higher.

Figure 8:
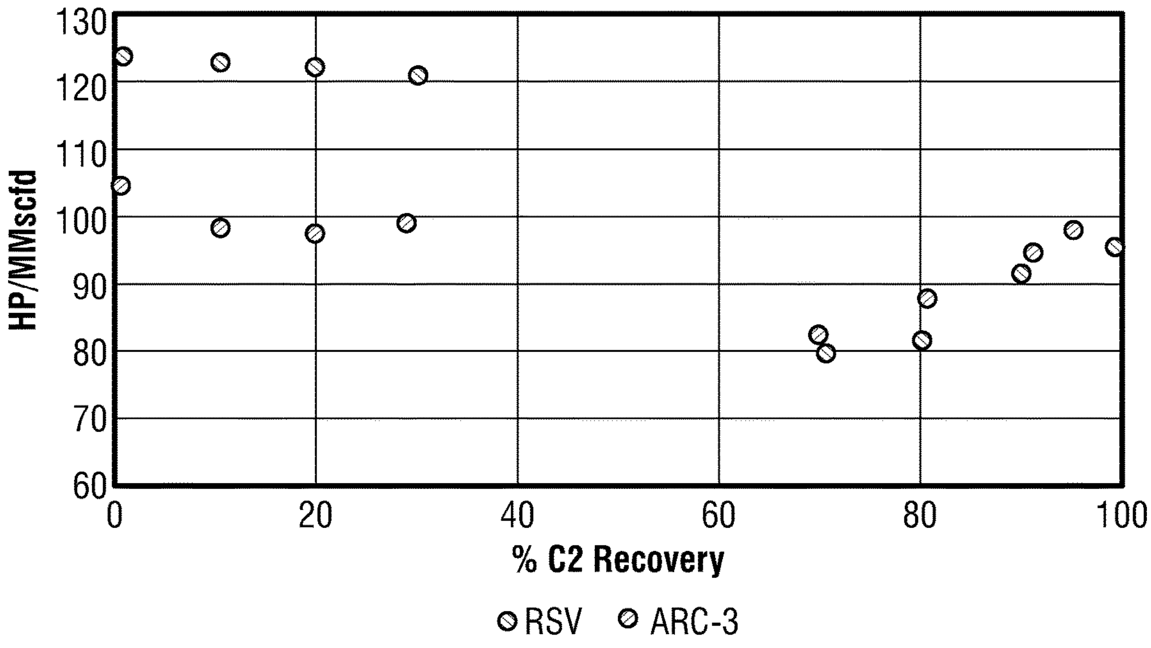
FIG. 8 is a graph of HP/MMscfd (y-axis) and % ethane recovery (x-axis) for different processes.

FIG. 8 is a graph of HP/MMscfd (y-axis) and ethane recovery (x-axis). In FIG. 8, the HP, per plant size, show an almost 20% increase in HP requirements in rejection cases to obtain the propane recoveries using RSV. In FIG. 8, the HP per gas plant nameplate shows and almost 20% increase in requirement in rejection for RSV plants to recover high propane, which can be less than, equal to, or slightly greater than the ARC-3 process recoveries.

Many plants use GSP process, while others use RSV. Operational troubles can sometimes cause the RSV recycle to completely shutdown, and the plant reverts to a GSP mode. The ARC-3 embodiment can be used as a retrofit for existing plants, and can facilitate debottlenecking capacity (e.g., a plant at 200 MMscfd flow can be debottlenecked easier at >200 with the ARC-3 retrofit installed).

In some embodiments, the components of the subsystems (e.g., subsystems 100, 200, 300, 400, and 500) can be designed and portions of the equipment utilized to run a plant in an RSV. Such a system can provide incremental ethane recovery in recovery mode (RSV), while requiring the addition of residue compression. Typical GSP recoveries are 90-94%, whereas if a plant is configured with equipment designed to run in RSV mode, the recoveries can be increased to 97-99%. In such a system, the entirety of the gas from the overheads of the main fractionator (e.g., 60) can form directed to a bottom of the second fractionator of the added subsystem. The residue gas can be cooled and become a reflux to the top of the second fractionator.

The enumerated concepts describe, and include within their descriptions, methods, processes, techniques, configurations, systems, apparatus, constructions, assemblies, subsystems and subprocesses and the like. This list should not be considered limiting, however, as, for example, the elements or features, in respect to system or configuration, may be combined with each of the other elements associated with other systems and configurations. The same applies to methods and various, exemplary steps.

The exemplary applications described herein include modifications to an NGL processing plant, and more particularly, techniques favoring the primary recovery of certain targeted hydrocarbons (e.g., from a demethanizer). The described methods and techniques, and system configurations and more detailed variations thereof are not limiting of the concepts. The concepts described herein contemplate, for example, implementation within other NGL processing systems and other recovery techniques for ethane, propane, butane, and/or other hydrocarbons to varying degrees.

The foregoing has been presented for purposes of illustration and description. These descriptions are not intended to limit the disclosure or aspects of the disclosure to the specific plants, systems, apparatus, methods, configurations, and processes disclosed. Various aspects of the disclosure are intended for applications other than the systems or the specific constitution and gas flows referred to above. As noted above, certain of the subprocesses and subsystems may, for example, be readily inserted and substituted in other, similar plant systems and processes. In other words, certain of the processing techniques and methods, and equipment configurations and designs described may also be incorporated into or with other hydrocarbon processing systems and processes. The disclosed systems and methods may also incorporate different components in alternate designs according to the present description. These and other variations of the disclosure will become apparent to one generally skilled in the relevant art provided with the present disclosure. Consequently, variations and modifications commensurate with the above teachings, and the skill and knowledge of the relevant art, are within the scope of the present disclosure. The embodiments described and illustrated herein are further intended to explain best or preferred modes for practicing the disclosure, and to enable others skilled in the art to utilize the disclosure and other embodiments and with various modifications required by the particular applications or uses of the present disclosure.

While specific embodiments and equipment are shown and described herein, one skilled in the art would understand that the methods, systems, and apparatus disclosed herein are not limited to these particular embodiments described. As one of ordinary skill in the art will readily appreciate from the disclosure, systems, processes, machines, configurations, constructions, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A system for separating a natural gas stream, the system comprising: a natural gas inlet;

a first fractionator including one or more inlets, wherein at least one of the inlets of the first fractionator is in fluid communication with the natural gas inlet, the first fractionator including a first vapor effluent outlet and a first liquid product outlet; and a second fractionator, the second fractionator including one or more inlets in fluid communication with the first vapor effluent outlet, the second fractionator including a second vapor effluent outlet and a second liquid product outlet, wherein the second liquid product outlet is directed to and, in fluid communication with, at least one of the inlets of the first fractionator; and wherein the second fractionator is positioned upstream of the first fractionator such that liquid product output of the second fractionator is directed into the first fractionator from the second liquid product outlet.

2. The system of claim 1, wherein the second vapor effluent outlet is in fluid communication with one of the inlets into the second fractionator.

3. The system of claim 2, further comprising a compressor fluidly coupled between the second vapor effluent outlet and the second fractionator.

4. The system of claim 1, wherein piping that is fluidly coupled between the first vapor effluent outlet and the inlets of the second fractionator fluidly couples with a bottom of the second fractionator and with a top of the second fractionator.

5. The system of claim 4, further comprising a vapor effluent heat exchanger fluidly coupled with both the second vapor effluent outlet of the second fractionator and said vapor fluid effluent outlet of the first fractionator and configured to pass vapor effluent streams from each of said first and second fractionators in thermal communication prior to said stream of second vapor effluent being passed to the first heat exchanger.

6. The system of claim 1, further comprising an expansion valve fluidly coupled between the second liquid outlet and one of the inlets of the first fractionator.

7. The system of claim 1, wherein the first fractionator is configured to operate at a first pressure, wherein the second fractionator is configured to operate at a second pressure, and wherein the first pressure is higher than the second pressure.

8. The system of claim 1, wherein, the first fractionator is a main fractionator;

the second fractionator is a secondary fractionator;

said effluent flow line is directed as an outlet of the main fractionator, said effluent line being further divided into a first flow line and a second flow line;

a vapor effluent heat exchanger disposed in fluid communication with said first flow line and intermediate said main and secondary fractionators such that a first stream exiting said heat exchanger discharges into an upper portion of the secondary fractionator;

wherein said second flow line communicates a second stream from the effluent flow into a lower portion of the secondary fractionator; and wherein a lower portion of the second fractionator is disposed in fluid communication with said first fractionator such that a stream containing fluids is communicated from the lower portion to the main fractionator.

9. A system for separating a natural gas stream, the system comprising:

a natural gas inlet;

a first fractionator including one or more inlets, wherein at least one of the inlets of the first fractionator is in fluid communication with the natural gas inlet, the first fractionator including a first vapor effluent outlet and a first liquid product outlet; and a second fractionator including one or more inlets in fluid communication with the first vapor effluent outlet, the second fractionator including a second vapor effluent outlet and a second liquid product outlet, wherein the second liquid product outlet is in fluid communication with at least one of the inlets of the first fractionator;

a heat exchanger positioned downstream from said second fractionator and said second vapor effluent outlet, the heat exchanger being configured in fluid communication with a fluid inlet stream from the natural gas inlet and passed as a fluid inlet stream into one of the inlets of the second fractionator, and such that a stream of said second vapor effluent stream is directed in thermal communication with a fluid inlet stream into the second fractionator; and wherein said first fractionator is a main fractionator, and said second fractionator is a second fractionator, further comprising:

the first effluent flow line being directed from the main fractionator and configured to discharge into a lower portion of the secondary fractionator;

the second effluent flow line being directed from an effluent outlet of the secondary fractionator, and further divided into a first flow line and a second flow line in fluid communication with an upper portion of the secondary fractionator;

a compressor disposed in said second flow line downstream of said effluent outlet;

a first heat exchanger disposed in fluid communication with said second flow line and intermediate said effluent outlet and an inlet into an upper portion of said secondary fractionator such that a first stream exiting said first heat exchanger discharges into an upper portion of the secondary fractionator via said inlet;

wherein said second flow line communicates a second stream from the effluent outlet into a lower portion of the secondary fractionator; and wherein a lower portion of the secondary fractionator is disposed in fluid communication with said main fractionator, such that a stream containing fluids is communicated from the lower portion of the secondary fractionator to the main fractionator.

10. The system of claim 9, wherein an inlet gas feed line passes through said first heat exchanger in heat transfer communication with said second stream and then into said secondary fractionator.

11. The system of claim 10, wherein said inlet gas feed line passes through a second heat exchanger in heat transfer communication with said first flow line prior to passing through said first heat exchanger, further comprising a chiller and a separator disposed downstream of said heat exchanger and in fluid communication with said second heat exchanger.

12. A system for separating a natural gas stream, the system comprising:

a natural gas inlet;

a first fractionator including one or more inlets, wherein at least one of the inlets of the first fractionator is in fluid communication with the natural gas inlet, the first fractionator including a first vapor effluent outlet and a first liquid product outlet; and a second fractionator, the second fractionator including one or more inlets in fluid communication with the first vapor effluent outlet, the second fractionator including a second vapor effluent outlet and a second liquid product outlet, wherein the second liquid product outlet is in fluid communication with at least one of the inlets of the first fractionator, wherein, the first fractionator is a main fractionator;

the second fractionator is a secondary fractionator;

said effluent flow line is directed as an outlet of the main fractionator, said effluent line being further divided into a first flow line and a second flow line;

a first heat exchanger disposed in fluid communication with said first flow line and intermediate said main and secondary fractionators such that a first stream exiting said heat exchanger discharges into an upper portion of the secondary fractionator;

wherein said second flow line communicates a second stream from the effluent flow into a lower portion of the secondary fractionator; and wherein a lower portion of the second fractionator is disposed in fluid communication with said first fractionator such that a stream containing fluids is communicated from the lower portion to the main fractionator.

13. The system of claim 1, further comprising a first heat exchanger configured in fluid communication with a fluid inlet stream directed from the natural gas inlet into the second fractionator such that a stream of said second vapor effluent is directed in thermal communication with the fluid inlet stream into the second fractionator.

14. The system of claim 13, further comprising a second heat exchanger fluidly coupled between the first vapor effluent outlet and at least one of the inlets of the second fractionator, wherein the second heat exchanger is configured to pass the fluid inlet stream into the second fractionator and at least a portion of the first vapor effluent stream such that said portion of the first vapor effluent stream and said fluid inlet stream are passed in thermal communication prior to being passed to the second fractionator; and wherein the first heat exchanger is configured in fluid communication with the fluid inlet stream from the natural gas inlet and with the second fractionator to pass said fluid inlet stream into one of the inlets of the second fractionator after said inlet stream passes in thermal communication with second vapor effluent.

15. The system of claim 14, wherein the first heat exchanger is fluidly coupled with the natural gas inlet.

16. The system of claim 14, wherein each of the heat exchangers is coupled in fluid communication with the natural gas inlet.

17. The system of claim 12, further comprising an inlet gas line and a second heat exchanger disposed intermediate said first heat exchanger and said inlet gas line and in fluid communication with said inlet gas line and said secondary fractionator; and wherein an effluent flow line directed outward from said secondary fractionator passes said second heat exchanger such that an inlet gas stream passes said first and second heat exchangers and passes in heat transfer communication with effluent flow in said effluent flow line from said second fractionator and effluent flow from said main fractionator prior to delivery into said main fractionator.

18. The system of claim 12, wherein both of said second flow line from said main fractionator and said inlet gas line, from said first heat exchanger, discharge into a lower portion of the secondary fractionator, and said first flow line, from said first heat exchanger, discharges into an upper portion of the secondary fractionator.

19. The system of claim 18, wherein an effluent flow line from said secondary fractionator passes through said first heat exchanger and in heat transfer communication with first flow line.

20. The system of claim 19, wherein said effluent flow line from said secondary fractionator passes from said heat transfer communication with said first heat exchanger outward from said secondary fractionator.

21. The system of claim 18, wherein an inlet gas feed line passes through said first heat exchanger prior to delivery into the lower portion of said secondary fractionator.

22. The system of claim 21, wherein said first heat exchanger is configured to pass said inlet gas feed line, said first flow line from said main fractionator, and an effluent flow line from said secondary fractionator; and wherein said effluent flow line from said secondary fractionator and said inlet gas feed line pass in cross flow heat transfer communication through a second heat exchanger disposed upstream of said first heat exchanger in respect to said inlet gas feed line and downstream of said first heat exchanger in respect to said effluent flow line from said secondary fractionator.

* * * * *